United States Patent
Castro

(10) Patent No.: US 11,246,631 B2
(45) Date of Patent: Feb. 15, 2022

(54) SURGICAL FASTENER

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 0 days.

(21) Appl. No.: 17/075,834

(22) Filed: Oct. 21, 2020

(65) Prior Publication Data

US 2021/0244452 A1 Aug. 12, 2021

Related U.S. Application Data

(60) Provisional application No. 62/975,248, filed on Feb. 12, 2020.

(51) Int. Cl.
| *A61B 17/16* | (2006.01) |
| *A61B 17/84* | (2006.01) |
| *A61B 17/70* | (2006.01) |
| *A61B 17/86* | (2006.01) |

(52) U.S. Cl.
CPC .......... *A61B 17/7055* (2013.01); *A61B 17/16* (2013.01); *A61B 17/7035* (2013.01); *A61B 17/84* (2013.01); *A61B 17/8605* (2013.01); *A61B 17/8625* (2013.01); *A61B 17/8635* (2013.01); *A61B 2017/8655* (2013.01)

(58) Field of Classification Search
CPC ..... A61B 17/16; A61B 17/70; A61B 17/7001; A61B 17/7032; A61B 17/7035; A61B 17/7055; A61B 17/7056; A61B 17/72; A61B 17/84; A61B 17/844; A61B 17/8605; A61B 17/8625; A61B 2017/8655

See application file for complete search history.

(56) References Cited

U.S. PATENT DOCUMENTS

| 5,258,002 | A | 11/1993 | Jeffers et al. |
| 6,083,238 | A | 7/2000 | Alexander, Jr. |
| 8,080,027 | B2 | 12/2011 | Kozlowski |
| 2013/0172917 | A1 | 7/2013 | Saito |
| 2020/0305896 | A1* | 10/2020 | Castro .................. A61B 17/84 |

* cited by examiner

*Primary Examiner* — Larry E Waggle, Jr.
(74) *Attorney, Agent, or Firm* — Business Patent Law, PLLC; Kenneth F. Pearce

(57) ABSTRACT

A surgical fastener for use in posterior surgeries that require fusion between the occiput and pelvis. Among other things, the surgical fastener includes a cutter for cutting bone or other tissue.

22 Claims, 4 Drawing Sheets

SURGICAL FASTENER

PRIORITY

Applicant claims the benefit of U.S. Provisional Application No. 62/975,248—Surgical Fastener—filed on Feb. 12, 2020.

BACKGROUND OF THE INVENTION

A. Field of the Invention

The present invention is a surgical fastener provided with an elongate blade having an anterior tapered tip, first and second cutters attached to a centralized segment of the elongate blade and a head. In select preferred embodiments, the head can be fixed or polyaxial. Except for the head, the surgical fastener is threadless.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 5,258,002—Jeffers, et al. discloses a dual tapered surgical knife; 2) U.S. Pat. No. 6,083,238—Alexander, Jr. discloses an apparatus and method for improved aortic incision; 3) U.S. Pat. No. 8,080,027—Kozlowski discloses a surgical knife blade with hollow bevel; and 4) U.S. Published Patent Application 20130172917—Saito discloses a medical knife.

Among other things, none of the above listed references, alone or in combination, disclose a surgical fastener comprising: a) an elongate blade comprising: i) a longitudinal axis; ii) an end wall perpendicular to the longitudinal axis; iii) an anterior tapered cutting tip opposite from the end wall; iv) relative to the longitudinal axis, a length greater than a width and a beveled segment, lateral from longitudinal axis, including the anterior tapered cutting tip and creating first and second opposed cutting edges; b) a first cutter attached to the first cutting edge and extending away from the longitudinal axis, wherein a contour of the first cutter distal from the longitudinal axis traverses a lengthwise plane of the elongate blade's first cutting edge; c) a second cutter attached to the second cutting edge and extending away from the longitudinal axis, wherein a contour of the second cutter distal from the longitudinal axis traverses a lengthwise plane of the elongate blade's second cutting edge; and d) a head connected to the end wall; the head adapted to receive an apparatus distinct from the surgical fastener.

SUMMARY OF THE INVENTION

Successful fusion of a joint or broken bone is directly correlated to the construct rigidity surrounding the area of interest. Current spinal instrumentation relies on screws being anchored into bone and rods connecting to these anchors. Loosening of current constructs occurs primarily at the bone-anchor interface. Toggling of the screws can allow for enlargement of the insertion pathway. As the diameter of the insertion pathway increases, there is greater risk of the screw backing out and construct failure. The current invention can be utilized for arthrodesis procedures of the cervical, thoracic and lumbar spine, as well as the sacroiliac joint or other similar joints.

The biomechanical strength of traditional threaded fixation screws is dependent upon several design characteristics. Larger diameter screws are stronger and more difficult to extract due to increased surface area (friction). The thread pitch, or difference between the inner diameter and the outer diameter, also influences resistance to pull out or back out. The larger the pitch, the greater is the resistance to pull out. Biomechanical studies have demonstrated that the volume of bone between screw threads can influence the screw's resistance to pull out. Those skilled in the art recognize that the type and quality of bone are important variables influencing resistance to pull out. Patients with osteoporotic bone have significantly less dense bone than patients with normal bone densities. The contribution of the cancellous bone between the screw threads in patients with osteoporosis is less than patients of normal bone density. In some osteoporotic patients, the screw's fixation strength and resistance to pull out can be determined by the volume of cortical bone in one or two threads of a traditional fixation screw.

Long surgical constructs, such as those used for scoliosis or deformity correction surgery, are often anchored into the sacrum or ilium. These constructs are usually anchored with a large diameter threaded screw. The biophysical forces transmitted to these implanted screws can lead to loosening, construct failure, pain and additional revision surgery.

Many of traditional surgical screws include thread lengths of one to two millimeters that determine the screw's fixation strength. The current surgical fastener provides a potential fixation surface area of from about three to about ten times more than traditional fixation screws. In use, the potential surface area of the surgical fastener is generally juxtaposed the cortical bone—the patient's strongest bone. The current invention can be provided with surface treatments and apertures that can encourage bone ingrowth, long-term construct stability and arthrodesis.

Preferred embodiments of the surgical fastener can include an anterior tapered tip, first and second cutters attached to an elongate blade and a head.

The anterior tapered tip can separate surfaces or a joint, such as the sacroiliac joint or posterior cervical joint or the frontal edge can cut cortical bone. When rotated, the surgical fastener can be adapted to cut cartilage, cortical bone or other tissues that can provide exposure of bone to another bony surface. Exposing two bony surfaces can increase the probability the bony surfaces uniting into a solid fusion. The cutter may facilitate reapproximation of two joint surfaces that have experienced a distractive deformity from trauma or tumor. Prior to cutting through the first articular surface, the cutter can guide the bone back towards its anatomic position. Once the cutter crosses both articular surfaces, forward pressure on the cutter compresses the two surfaces and the barbs prevent retropulsion. When a cutter is placed across a joint, it may also facilitate fusion by exposing a conduit for bone to form across the joint. When the cutter is positioned completely across a joint, it may compress the articular or bony surfaces. Such imposed motion limitation may result in joint ankylosis.

Among other things, the surgical fastener's head can: limit the depth the fastener can be inserted through the incision into the surgically created cavity or joint space; be connected with other surgical apparatus, such as, rods, plates or other fixation devices; and relative to a headless screw, apply increased torque to the cutter.

Intentional or unintentional rotation of threaded devices can lead to displacement of the device into or towards an undesirable location resulting in damage or dysfunction to either a nerve or blood vessel. Those skilled in the art recognize that expulsion of a surgical screw results in an unstable screw that can increase the risk of non-fusion or spinal deformity. Among other things, the surgical fastener can be provided with a head of sufficient area to prevent over-insertion into the surgically created cavity or joint space. Depending on medical and/or surgical parameters, the current invention can be adapted to either compress or distract a joint. By way of illustration, when distraction of the posterior cervical facet joint occurs, the adjacent neuroforamin is enlarged and indirect decompression of the exiting nerve root can occur. According to the current state-of-the art, threaded surgical screws cannot provide this benefit.

Subsequent to insertion into a surgically created cavity or joint space with adequate outward tissue remaining proximate the insertion point, rotating the surgical fastener from about from about 30 degrees to about 150 degrees can improve the surgical fastener's resistance to pull out forces.

An aspect of the present invention is to provide a surgical fastener.

Still another aspect of the present invention is to provide a surgical fastener with an anterior tapered tip and a head opposite the anterior tapered tip.

It is yet another aspect of the present invention to provide a surgical fastener with either a fixed head or a polyaxial head.

Still another aspect of the present invention is to provide a surgical fastener with a receptacle or a receiver adapted to receive an apparatus distinct from the surgical fastener.

It is still another aspect of the present invention to provide a surgical fastener with first and second cutters.

Yet still another aspect of the present invention is to provide a surgical fastener with an elongate blade.

A preferred embodiment of the current invention can be described as a surgical fastener comprising: a) an elongate blade comprising: i) a longitudinal axis; ii) an end wall perpendicular to the longitudinal axis; iii) relative to the longitudinal axis, a length greater than a width and a first thickness of a centralized segment thicker than a second thickness of a peripheral segment lateral from the centralized segment; iv) an anterior tapered cutting tip opposite from the end wall; the anterior tapered cutting tip comprising first and second sloped edges relative to the centralized segment; v) a first cutting edge comprising a first bevel relative to the centralized segment; and vi) a second cutting edge comprising a second bevel relative to the centralized segment, wherein the anterior cutting tip, the first bevel and second bevel form a continuous periphery; b) a first cutter attached to the first cutting edge and extending away from the longitudinal axis, wherein a contour of the first cutter distal from the longitudinal axis traverses a lengthwise plane of the elongate blade's first cutting edge; c) a second cutter attached to the second cutting edge and extending away from the longitudinal axis, wherein a contour of the second cutter distal from the longitudinal axis traverses a lengthwise plane of the elongate blade's second cutting edge; and d) a receiver positioned in the end wall; the receiver adapted to receive an apparatus distinct from the surgical fastener.

Another preferred embodiment of the current invention can be described as a surgical fastener comprising: a) an elongate blade comprising: i) a longitudinal axis; ii) an end wall perpendicular to the longitudinal axis; iii) relative to the longitudinal axis, a length greater than a width and a first thickness of a centralized segment thicker than a second thickness of a peripheral segment lateral from the centralized segment; iv) an anterior tapered cutting tip opposite from the end wall; the anterior tapered cutting tip comprising first and second sloped edges relative to the centralized segment; v) a first cutting edge comprising a first bevel relative to the centralized segment; and vi) a second cutting edge comprising a second bevel relative to the centralized segment, wherein the anterior cutting tip, the first bevel and second bevel form a continuous periphery; b) a first cutter attached to the first cutting edge and extending away from the longitudinal axis, wherein a contour of the first cutter distal from the longitudinal axis traverses a lengthwise plane of the elongate blade's first cutting edge; c) a second cutter attached to the second cutting and extending away from the longitudinal axis, wherein a contour of the second cutter distal from the longitudinal axis traverses a lengthwise plane of the elongate blade's second cutting edge; and d) a head connected to the end wall; the head adapted to receive an apparatus distinct from the surgical fastener.

Yet still another preferred embodiment of the current invention can be described as a surgical fastener comprising: a) an elongate blade comprising: i) a longitudinal axis; ii) an end wall perpendicular to the longitudinal axis; iii) an anterior tapered cutting tip opposite from the end wall; iv) relative to the longitudinal axis, a length greater than a width and a beveled segment, lateral from longitudinal axis, including the anterior tapered cutting tip and creating first and second opposed cutting edges; b) a first cutter attached to the first cutting edge and extending away from the longitudinal axis, wherein a contour of the first cutter distal from the longitudinal axis traverses a lengthwise plane of the elongate blade's first cutting edge; c) a second cutter attached to the second cutting edge and extending away from the longitudinal axis, wherein a contour of the second cutter distal from the longitudinal axis traverses a lengthwise plane of the elongate blade's second cutting edge; and d) a head connected to the end wall; the head adapted to receive an apparatus distinct from the surgical fastener.

It is the novel and unique interaction of these simple elements which creates the system within the ambit of the present invention. Pursuant to United States Code, select preferred embodiments of the current invention follow. However, it is to be understood that the descriptions of the preferred embodiments do not limit the scope of the present invention.

DESCRIPTION OF THE PREFERRED EMBODIMENTS

Figure 1:
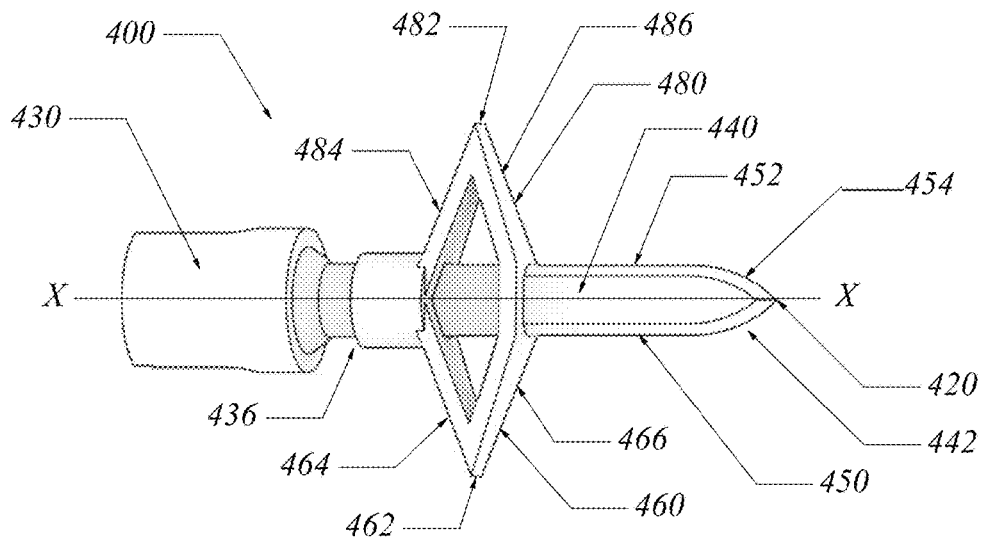
FIG. 1 is a perspective of a first preferred embodiment of surgical fastener (400) including opposed first and second cutters.
Figure 1A:
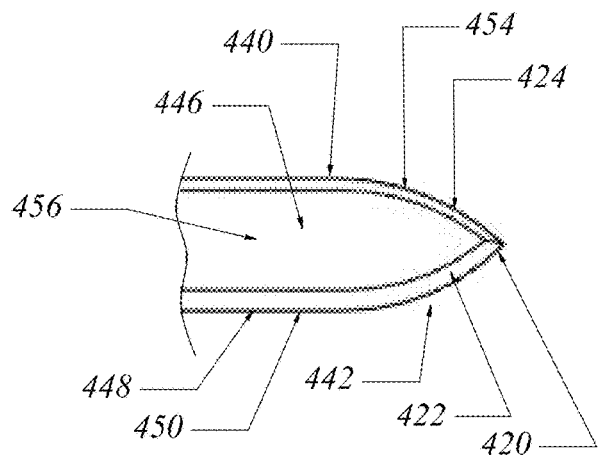
FIG. 1a is a second perspective of the FIG. 1 preferred embodiment of surgical fastener (400) where surgical fastener (400) was rotated approximately 90 degrees.
Figure 2:
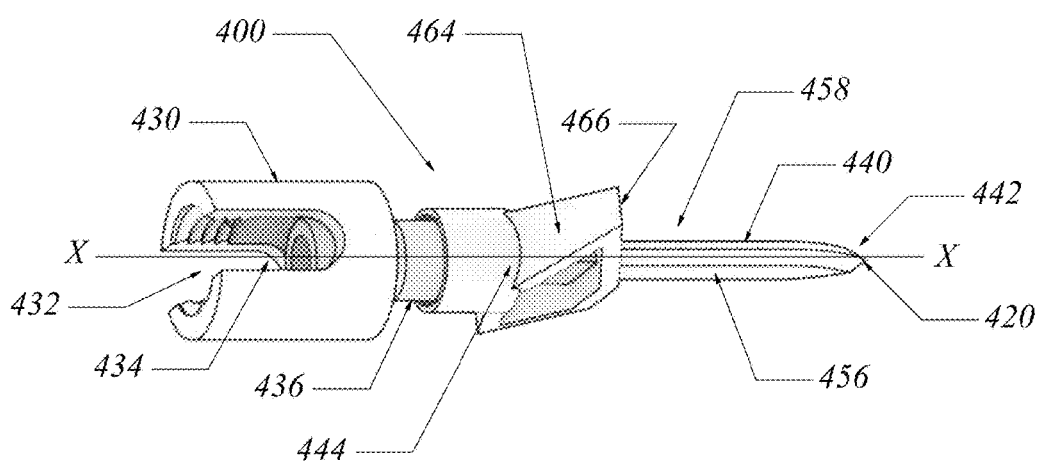
FIG. 2 is a perspective of anterior end (442) of elongate blade (440) of surgical fastener (400).

Although the disclosure hereof is detailed to enable those skilled in the art to practice the invention, the embodiments published herein merely exemplify the present invention.

As used herein, with respect to the surgical fastener (400): 1) "anterior" of the surgical fastener (400) means the side of the surgical fastener most distant from the surgeon and 2) "posterior or surgeon-facing side" of the surgical fastener (400) means the side of the surgical fastener nearest the surgeon.

In the most general sense, the present invention can result in joint arthrodesis where the surgical fastener is surgically inserted into or across a joint space. Depending on surgical parameters one or more surgical fasteners can be associated with the same surgically created cavity or joint space. The current surgical fastener can be useful for surgeries that can assist in stabilizing injured, deformed and or degenerative joints. Preferred embodiments of the current invention can be employed with ankle, cervical, hand, skull, sacroiliac or other orthopaedic procedures. It appears that the present system is particularly useful for posterior fusions from the occipital region to the pelvis, including the sacroiliac joints. However, the current invention can also be used to fuse the tibia to the talus, the talus to the calcaneus, and metacarpals to the phalanges.

Preferred embodiments of the current surgical fasteners can be manufactured of titanium alloys, stainless steel, non-resorbable polymers or any other composition acceptable in the art. Meeting a long felt but unfilled need in the orthopaedic surgical arts, the novel and unique structures of the present surgical fastener allow the surgical team to, among other things, simplify previous procedures.

The present invention has an anterior side with an anterior tapered cutting tip extending from an anterior end of the elongate blade, one or more cutters attached to the elongate blade and a head attached to the posterior side of the elongate blade, all of which coincide with the longitudinal axis of the surgical fastener. The anterior edge of the surgical fastener is capable of dissecting through adipose, muscle, bone, and/or joint capsule tissues. Relative to the longitudinal axis, the elongate blade is rotatable and can include a length greater than a width and a first thickness of a centralized segment thicker than a second thickness of a peripheral segment lateral from the centralized segment.

The cutters of the surgical fastener are capable of cutting cartilage and bone and can be associated with the creation of the surgical cavity. In select preferred embodiments, cutters can include a noncutting edge or margin. However, other preferred embodiments of the cutters can cut in a clockwise or counterclockwise direction or both directions. Further, the rotatable cutters can morselize bone in preparation for fusion.

In a preferred embodiment of the surgical fastener, the elongate blade can be provided with opposed cutters. The first cutter includes an angled surgeon facing surface relative to the first cutting edge of the elongate blade and an angled anterior facing surface relative to the first cutting edge and the second cutter includes an angled surgeon facing surface relative to the second cutting edge of the elongate blade and an angled anterior facing surface relative to the second cutting edge. In this preferred embodiment, the angled surgeon facing surface and anterior facing surface of each cutter intersect creating first and second distal contours of the first and the second cutters. First distal and second distal contours are perpendicular to their respective first and second cutting edges. The attachment angles of the cutters are measured from the longitudinal axis proximate the head of the surgical fastener or receiver of the elongate blade to the distal contours of the cutters. Because of the intersection of the angled surgeon facing surface and the angled anterior facing surface of the cutter, a multiplanar cutter can be formed.

In another preferred embodiment of the surgical fastener, the elongate blade can be provided with opposed cutters. The first cutter includes a perpendicular surgeon facing surface relative to the first cutting edge of the elongate blade and an angled anterior facing surface relative to the first cutting edge and the second cutter includes a perpendicular surgeon facing surface relative to the second cutting edge of the elongate blade and an angled anterior facing surface relative to the second cutting edge. In this preferred embodiment, the perpendicular surgeon facing surface and the angled anterior facing surface intersect creating distal contours of the first and the second cutters. First distal and second distal contours traverse their respective first and second cutting edges. The attachment angles of the cutters are measured from the longitudinal axis proximate the head of the surgical fastener or receiver of the elongate blade to the distal contours of the cutters. In this preferred embodiment the attachment angles of the cutters range from about 90 degrees to about 120 degrees. Because of the intersection of the perpendicular surgeon facing surface and the angled anterior facing surface of the cutter, a multiplanar cutter can be formed.

In still another preferred embodiment of the surgical fastener, the elongate blade can be provided with opposed wing-like cutters. A first cutter is attached to a first cutting edge of the elongate blade and a second cutter is attached to a second cutting edge of the elongate blade. In this embodiment, the distal tip, traverses its respective cutting edge, of each wing-like cutter is also the distal contour of the cutter. The attachment angles of the wing-like cutters are measured from the longitudinal axis proximate the head of the surgical fastener or receiver of the elongate blade to the distal contours of the cutters. In this preferred embodiment the attachment angles of the cutters range from about 90 degrees to about 120 degrees.

A head can be connected to the surgeon facing side of the elongate blade. The head can be provided with a receptacle and slots adapted to receive an apparatus distinct from the surgical fastener. Some preferred embodiments include an extender connecting the head to the elongate blade. Depending on surgical requirements, the head can be either fixed or polyaxial. And still other embodiments of the elongate blade can be provided with a receiver adapted to receive an apparatus distinct from the surgical fastener.

The combination of the anterior tapered cutting tip, elongate blade, cutters and head of the surgical fastener meet long felt but unfilled needs in the orthopedic surgical arts of, among other things, allowing the surgeon to simplify the previous operating procedures utilized for posterior cervical, sacroiliac, and other joint fusions.

FIGS. 1-5 are perspectives of preferred embodiments of surgical fastener (400). Among other things, surgical fastener (400) can include anterior tapered cutting tip (420), head (430), receiver (445), elongate blade (440), first cutter (460) and second cutter (480).

Anterior tapered cutting tip (420) is positioned at the anterior end (442) of elongate blade (440). Anterior tapered cutting tip (420) is provided with first and second sloped edges (422, 424) relative to centralized segment (446) of elongate blade (440). Depending on surgical parameters, sloped edges (422, 424) can be provided with a finish ranging from dull to sharp.

Head (430) is connected to end wall (444), opposed from anterior or first end (442) of elongate blade (440). Head (430) is provided with receptacle (432) adapted to receive an apparatus (not shown) distinct from surgical fastener (400). Receptacle (432) can be provided with one or more slots (434). Examples of apparatus received by receptacle (432) include insertion drivers that can advance the surgical fastener into or across a joint space, rods used to connect fasteners positioned at other spinal levels, and removal tools if surgical revision is required. Preferred embodiments of the current surgical fastener (400) can include fixed or polyaxial heads (430). When a polyaxial head (430) is utilized, an extender (436) extending from polyaxial head (430) and connected to end wall (444) of elongate blade (440) can expand the multiplanar range of polyaxial head (430).

Elongate blade (440) includes a longitudinal axis X-X, centralized segment (446) and peripheral segment (448) lateral from centralized segment (446). Relative to longitudinal axis X-X, elongate blade (440) has a length greater than a width and a first thickness of centralized segment (446) that is thicker than a second thickness of peripheral segment (448). First tapered cutting edge (450) is provided with a bevel relative to centralized segment (446). Second tapered cutting edge (452) is provided with a bevel relative to centralized segment (446). In select preferred embodiments of surgical fastener (400), anterior tapered cutting tip (420), first cutting edge (450) and second cutting edge (452) form continuous periphery (454), In select preferred embodiments, first cutter (460) is connected with first cutting edge (450) of elongate blade (440) and second cutter (480) is connected with second cutting edge (452) of elongate blade (440). Relative to longitudinal axis X-X, first distal contour (462) of first cutter (460) and second distal contour (482) of second cutter (480) traverse the lengthwise plane of elongate blade's (440) first and second cutting edges (450, 452).

In a preferred embodiment of surgical fastener (400), first cutter (460) is provided with an angled or perpendicular surgeon facing surface (464) relative to first cutting edge (450) and an angled anterior facing surface (466) relative to first cutting edge (450). Angled or perpendicular surgeon facing surface (464) and angled anterior facing surface (466) intersect to create first distal contour (462) of first cutter (460). Lateral margins of angled surgeon facing surface (464) and angled anterior facing surface (466) can provide the sharp cutting surfaces for first cutter (460). Second cutter (480) is provided with an angled or perpendicular surgeon facing surface (484) relative to second cutting edge (452) and an angled anterior facing surface (486) relative to second cutting edge (452). Angled or perpendicular surgeon facing surface (484) and angled anterior facing surface (486) intersect to create second distal contour (482) of second cutter (480). Lateral margins of angled surgeon facing surface (484) and angled anterior facing surface (486) can provide the sharp cutting surfaces for second cutter (480). As previously indicated, attachment angles of the surgeon facing surfaces (464, 484) to first and second cutting edges (450, 452) are measured from the longitudinal axis proximate head (430) or receiver (445) of surgical fastener (400) to the contours (462, 482), distal from the longitudinal axis, of first and second cutters (460, 480). Although not shown in FIGS. 1-2, those skilled in the art recognize that perpendicular or approximately perpendicular surgeon facing surfaces (464, 484) fall within the range of attachment angles of from about 90 degrees to about 120 degrees disclosed with respect to angled surgeon facing surfaces (464, 484).

Figure 3:
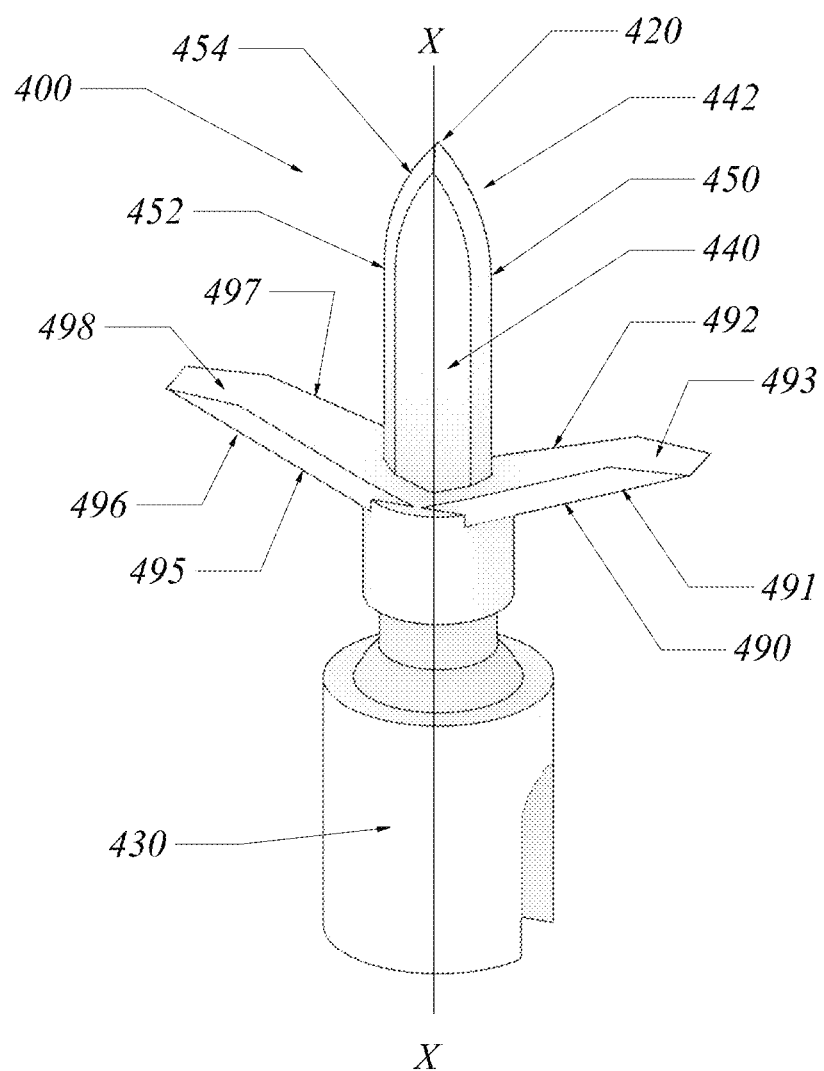
FIG. 3 is a perspective of a second embodiment of surgical fastener (400) including opposed first and second cutters.

With reference to FIG. 3, in a preferred embodiment of surgical fastener (400), first cutter (490) is provided with an angled surgeon facing surface (491) and opposed surface (492) connected to first cutting edge (450) of elongate blade (440). Distal contour (493) of first cutter (490) traverses the lengthwise plane of first cutting edge (450). Second cutter (495) is provided with an angled surgeon facing surface (496) and opposed surface (497) connected to second cutting edge (452). Distal contour (498) of second cutter (495) traverses the lengthwise plane of second cutting edge (452) of elongate blade (440). Lateral margins of first cutter (490) and second cutter (495) can provide the sharp cutting surfaces for first cutter (460) and second cutter (495). As previously indicated, attachment angles of the surgeon facing surfaces (491, 496) to first cutting edge (450) and second cutting edge (452) are measured from the longitudinal axis proximate head (430) or receiver (445) of surgical fastener (400) to contours (493, 498), distal from the longitudinal axis, of first and second cutters (490, 495). In this preferred embodiment the attachment angles of the cutters range from about 90 degrees to about 120 degrees.

Figure 4:
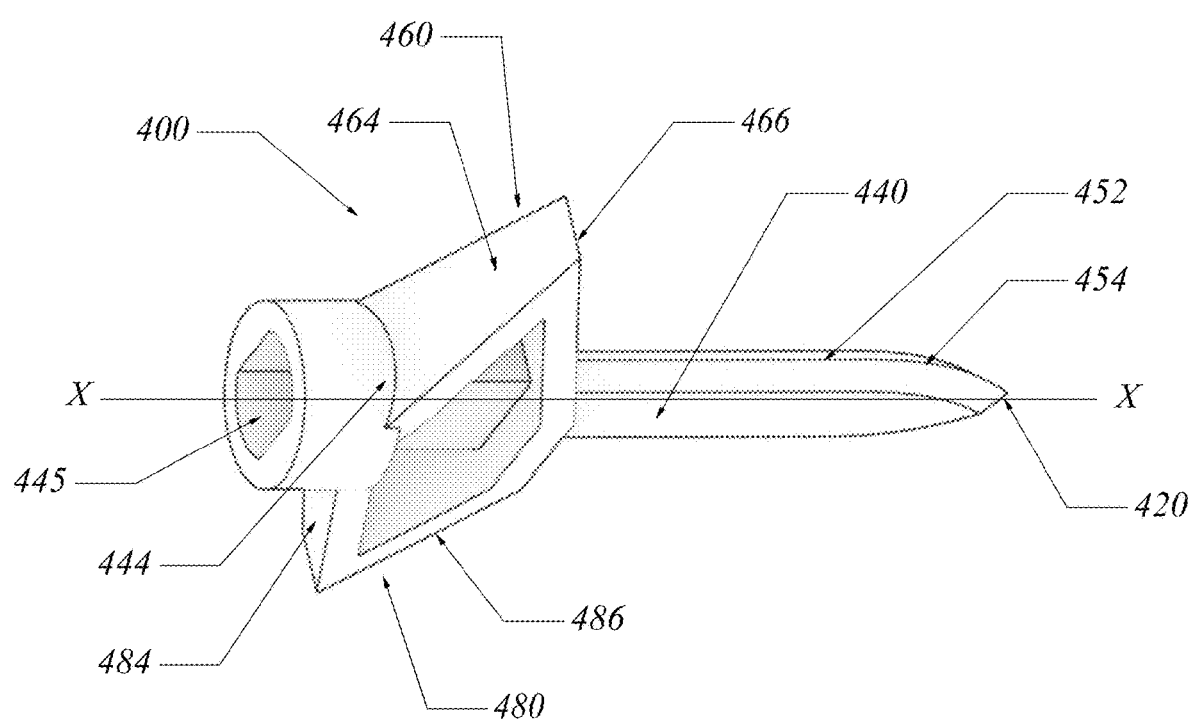
FIG. 4 is a perspective of a third embodiment of surgical fastener (400) including a receiver (445).
Figure 5:
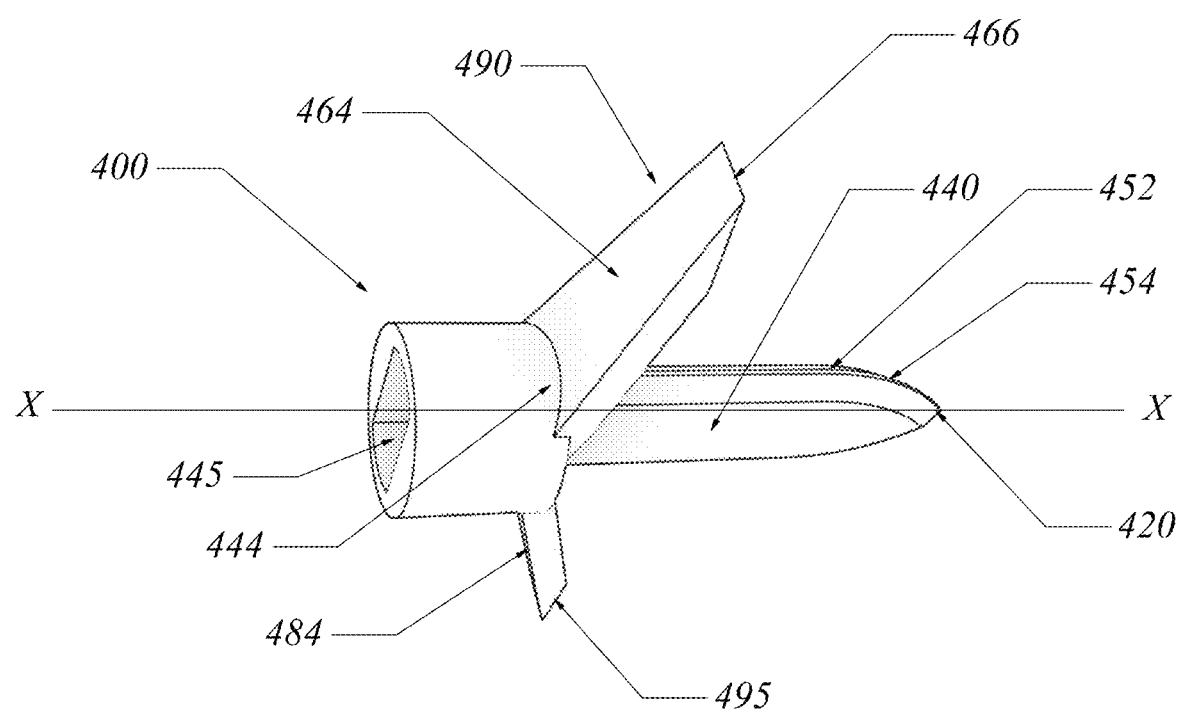
FIG. 5 is a perspective of a fourth embodiment surgical fastener including a receiver (445).

With reference to FIGS. 4 and 5, select preferred embodiments of surgical fastener (400) can be provided with receiver (445) at end wall or surgeon facing end (444) of elongate blade (440). Receiver (445) is adapted to receive an apparatus distinct from the surgical fastener (400). Use of receiver (445) eliminates the use of head (430) in utilization of the surgical fastener (400).

After insertion of the surgical fastener (400) through a surgical incision (not shown), engagement of the surgically created cavity or joint space (not shown) by the surgical fastener (400) and subsequent rotation of from about 30 degrees to about 150 degrees of elongate blade (440) relative to an engagement point of the surgically created cavity or joint space by anterior tapered cutting tip (420), surgical fastener (400) is positioned to resist pull out of surgical fastener (400) from the surgically created cavity or joint space.

Select preferred embodiments of the current invention have been disclosed and enabled as required by Title 35 of the United States Code.

What is claimed is:

1. A surgical fastener comprising:
   a) an elongate blade comprising:
      i) a longitudinal axis;
      ii) an end wall perpendicular to the longitudinal axis;
      iii) relative to the longitudinal axis, a length greater than a width and a first thickness of a centralized segment thicker than a second thickness of a peripheral segment lateral from the centralized segment;
      iv) an anterior tapered cutting tip opposite from the end wall; the anterior tapered cutting tip comprising first and second sloped edges relative to the centralized segment;
      v) a first cutting edge comprising a first bevel relative to the centralized segment; and
      vi) a second cutting edge comprising a second bevel relative to the centralized segment, wherein the anterior cutting tip, the first bevel and second bevel form a continuous periphery;
   b) a first cutter attached to the first cutting edge and extending away from the longitudinal axis, wherein a contour of the first cutter distal from the longitudinal axis traverses a lengthwise plane of the elongate blade's first cutting edge;
   c) a second cutter attached to the second cutting edge and extending away from the longitudinal axis, wherein a contour of the second cutter distal from the longitudinal axis traverses a lengthwise plane of the elongate blade's second cutting edge; and d) a receiver positioned in the end wall; the receiver adapted to receive an apparatus distinct from the surgical fastener.

2. The surgical fastener of claim 1, wherein surgeon facing surfaces of each cutter are connected to their respective first and second cutting edges at an attachment angle of from about 90 degrees to about 120 degrees.

3. The surgical fastener of claim 2, wherein after insertion through a surgical incision, engagement of a surgically created cavity or joint space by the surgical fastener and subsequent rotation of from about 30 degrees to about 150 degrees of the elongate blade relative to an engagement point of the anterior tapered cutting tip, the surgical fastener is positioned to resist pull out of the surgical fastener from the surgically created cavity or joint space.

4. The surgical fastener of claim 3, wherein the first cutter and the second cutter are adapted to cut in a clockwise, a counterclockwise or both directions.

5. The surgical fastener of claim 3, wherein lateral margins of at least one of the cutters comprises sharp cutting surfaces.

6. The surgical fastener of claim 5, wherein, each cutter comprises a perpendicular or approximately perpendicular surgeon facing surface and an angled anterior facing surface intersecting with the perpendicular or approximately perpendicular surgeon facing surface creating the distal contours of the cutters.

7. The surgical fastener of claim 5, wherein each cutter comprises an angled surgeon facing surface and an opposed surface creating the distal contours.

8. A surgical fastener comprising:
a) an elongate blade comprising:
   i) a longitudinal axis;
   ii) an end wall perpendicular to the longitudinal axis;
   iii) relative to the longitudinal axis, a length greater than a width and a first thickness of a centralized segment thicker than a second thickness of a peripheral segment lateral from the centralized segment;
   iv) an anterior tapered cutting tip opposite from the end wall; the anterior tapered cutting tip comprising first and second sloped edges relative to the centralized segment;
   v) a first cutting edge comprising a first bevel relative to the centralized segment; and
   vi) a second cutting edge comprising a second bevel relative to the centralized segment, wherein the anterior cutting tip, the first bevel and second bevel form a continuous periphery;
b) a first cutter attached to the first cutting edge and extending away from the longitudinal axis, wherein a contour of the first cutter distal from the longitudinal axis traverses a lengthwise plane of the elongate blade's first cutting edge;
c) a second cutter attached to the second cutting and extending away from the longitudinal axis, wherein a contour of the second cutter distal from the longitudinal axis traverses a lengthwise plane of the elongate blade's second cutting edge; and
d) a head connected to the end wall; the head adapted to receive an apparatus distinct from the surgical fastener.

9. The surgical fastener of claim 8 comprising an extender connecting the head to the end wall.

10. The surgical fastener of claim 9, wherein surgeon facing surfaces of each cutter are connected to their respective first and second cutting edges at an attachment angle of from about 90 degrees to about 120 degrees.

11. The surgical fastener of claim 10, wherein after insertion through a surgical incision, engagement of a surgically created cavity or joint space by the surgical fastener and subsequent rotation of from about 30 degrees to about 150 degrees of the elongate blade relative to an engagement point of the anterior tapered cutting tip, the surgical fastener is positioned to resist pull out of the surgical fastener from the surgically created cavity or joint space.

12. The surgical fastener of claim 11, wherein the first cutter and the second cutter are adapted to cut in a clockwise, a counterclockwise or both directions.

13. The surgical fastener of claim 12, wherein lateral margins of at least one of the cutters comprises sharp cutting surfaces.

14. The surgical fastener of claim 13, wherein the head is a polyaxial head.

15. The surgical fastener of claim 13, wherein, each cutter comprises a perpendicular or approximately perpendicular surgeon facing surface and an angled anterior facing surface intersecting with the perpendicular or approximately perpendicular surgeon facing surface creating the distal contours of the cutters.

16. The surgical fastener of claim 13, wherein each cutter comprises an angled surgeon facing surface and an opposed surface creating the distal contours.

17. A surgical fastener comprising:
a) an elongate blade comprising:
   i) a longitudinal axis;
   ii) an end wall perpendicular to the longitudinal axis;
   iii) an anterior tapered cutting tip opposite from the end wall;
   iv) relative to the longitudinal axis, a length greater than a width and a beveled segment, lateral from longitudinal axis, including the anterior tapered cutting tip and creating first and second opposed cutting edges;
b) a first cutter attached to the first cutting edge and extending away from the longitudinal axis, wherein a contour of the first cutter distal from the longitudinal axis traverses a lengthwise plane of the elongate blade's first cutting edge;
c) a second cutter attached to the second cutting edge and extending away from the longitudinal axis, wherein a contour of the second cutter distal from the longitudinal axis traverses a lengthwise plane of the elongate blade's second cutting edge; and
d) a head connected to the end wall; the head adapted to receive an apparatus distinct from the surgical fastener.

18. The surgical fastener of claim 17, wherein:
a) surgeon facing surfaces of each cutter are connected to their respective first and second cutting edges at an attachment angle of from about 90 degrees to about 120 degrees; and
b) after insertion through a surgical incision, engagement of a surgically created cavity or joint space by the surgical fastener and subsequent rotation of from about 30 degrees to about 150 degrees of the elongate blade relative to an engagement point of the anterior tapered cutting tip, the surgical fastener is positioned to resist pull out of the surgical fastener from the surgically created cavity or joint space.

19. The surgical fastener of claim 18, wherein:
a) the first cutter and the second cutter are adapted to cut in a clockwise, a counterclockwise or both directions; and
b) lateral margins of at least one of the cutters comprises sharp cutting surfaces.

20. The surgical fastener of claim 19, wherein the head is a polyaxial head.

21. The surgical fastener of claim 18, wherein the surgeon facing surfaces and angled anterior facing surfaces of each cutter create the distal contours of the cutters.

22. The surgical fastener of claim 21, wherein, each cutter comprises a perpendicular or approximately perpendicular surgeon facing surface.

* * * * *